United States Patent [19]

Wu

[11] 4,257,966
[45] Mar. 24, 1981

[54] PREPARATION OF VICINAL EPOXIDES

[75] Inventor: Yulin Wu, Bartlesville, Okla.

[73] Assignee: Phillips Petroleum Company, Bartlesville, Okla.

[21] Appl. No.: 73,819

[22] Filed: Sep. 10, 1979

Related U.S. Application Data

[62] Division of Ser. No. 934,667, Aug. 17, 1978, which is a division of Ser. No. 845,183, Oct. 25, 1977, Pat. No. 4,111,965, which is a division of Ser. No. 459,628, Apr. 10, 1974, Pat. No. 4,069,234.

[51] Int. Cl.$^3$ ............................................. C07D 301/02
[52] U.S. Cl. .......................... 260/348.16; 260/348.11; 260/348.55
[58] Field of Search ................................... 260/348.16

[56] References Cited

U.S. PATENT DOCUMENTS 2,856,413  10/1958  Malkemus et al. .............. 260/348.16

FOREIGN PATENT DOCUMENTS 845937  8/1952  Fed. Rep. of Germany ...... 260/348.16

Primary Examiner—Norma S. Milestone

[57] ABSTRACT

Vicinal epoxides having 2 to 30 carbon atoms per molecule are prepared by heating the corresponding carbonate esters having the general formula

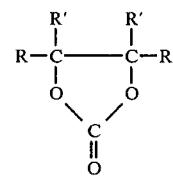

in the presence of a catalytic amount of a catalyst selected from the group consisting of phosphonium halides, sulfonium halides, sulfoxonium halides and metal salts selected from the group consisting of the halides, sulfates and carboxylates having 1 to 20 carbon atoms of iron, tin, manganese and zinc.

6 Claims, No Drawings

PREPARATION OF VICINAL EPOXIDES

This is a divisional application of application Ser. No. 934,667, filed Aug. 17, 1978, which is a division of Ser. No. 845,183, filed Oct. 25, 1977, now U.S. Pat. No. 4,111,965, which is a divisional of application Ser. No. 459,628, filed Apr. 10, 1974, now U.S. Pat. No. 4,069,234.

This invention relates to the preparation of vicinal epoxides.

Vicinal eposides are well known in the art as monomers in the preparation of resins of various types ranging from epoxy adhesive applications to elastomeric solvent-resistant polymers for use in making tubing, shoe soles and the like. Such epoxides can be prepared by the direct oxidation of an olefin or by treatment of the corresponding halohydrin with lime.

It is an object of this invention to provide a novel process for the preparation of vicinal epoxides.

Other objects, aspects and advantages of the invention will become obvious from the following description and the appended claims.

In accordance with the present invention, it has been discovered that vicinal epoxides having 2 to 30 carbon atoms per molecule having the general formula

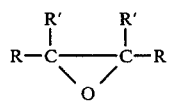

wherein each R and each R' are individually selected from the group consisting of hydrogen and hydrocarbyl radical groups having 1 to 10 carbon atoms and wherein both R' radicals can represent a divalent aliphatic hydrocarbon radical which together with the oxirane group

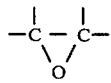

in said epoxide can form a cycloaliphatic nucleus, are prepared by heating the corresponding carbonate ester, having the general formula

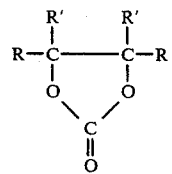

wherein R and R' are as defined above, in the presence of a catalytic amount of a catalyst selected from the group consisting of phosphonium halides, sulfonium halides, sulfoxonium halides and certain metal salts, each as hereinafter defined, under epoxide forming conditions. As used herein, the term "hydrocarbyl" includes alkyl, cycloalkyl, aryl, aralkyl and alkaryl radical groups.

The carbonate esters from which the vicinal epoxides are prepared according to the process of the present invention are the carbonate esters of vicinal diols containing from 2 to 30 carbon atoms per molecule and corresponding to the general formula

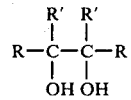

wherein each R and R' are hydrogen or a hydrocarbyl radical having from 1 to 10 carbon atoms.

Examples of suitable carbonate esters which can be employed in the process of this invention include the cyclic carbonate esters of the following vicinal diols: 1,2-ethanediol; 1,2-propanediol; 1,2,3,4-tetrahydro-1,2-naphthalenediol; 3,3-dimethylcyclobutane-1,2-diol; 3,3,4,4-tetramethylcyclobutane-1,2-diol; 2,3-dimethyl-2,3-butanediol; 2-methyl-2,3-butanediol; 2-methyl-1,2-propanediol; 2,3-butanediol; 2-phenyl-1,2-ethanediol; 1,2-butanediol; 1,2-pentanediol; 1-phenyl-1,2-butanediol; 2-phenyl-1,2-pentanediol; and 1-(2-methylphenyl)cyclohexane-1,2-diol.

The carbonate esters of vicinal diols are well known in the art. Such esters can be prepared by the reaction of a vicinal chlorohydrin with an alkali metal carbonate, bicarbonate or sesquicarbonate under pressure of carbon dioxide as disclosed in U.S. Pat. No. 2,766,258, J. D. Malkemus, issued Oct. 9, 1956. Such esters can also be prepared by the rection of a vicinal chlorohydrin with an alkali metal alkyl carbonate as disclosed in U.S. Pat. No. 2,784,201, H. C. Chitwood, issued Mar. 5, 1957.

Catalysts suitable for use in the process of this invention are selected from one of the following:

A. phosphonium halides having the formula R''₄PX, wherein R'' is selected from the group consisting of hydrogen, alkyl, cycloalkyl, aryl, alkenyl, cycloalkenyl and combinations thereof having from 1 to 10 carbon atoms and X is a halide selected from the group consisting of chlorine, bromine and iodine;

B. sulfonium halides having the formula R''₃SX wherein R'' and X are as given above;

C. sulfoxonium halides having the formula (R''₃S→O)+X— wherein R'' and X are as given above; and D. metal salts selected from the group consisting of the halides, sulfates and carboxylates having 1 to 20 carbon atoms of iron, tin, manganese and zinc.

Examples of suitable catalysts include methyltriphenylphosphonium bromide, ethyltriphenylphosphonium bromide, tetrabutylphosphonium bromide, tetrabutylphosphonium chloride, tetraphenylphosphonium bromide, tetraphenylphosphonium chloride, triphenylbenzylphosphonium chloride, allyldiethylsulfonium chloride, allyldimethylsulfonium bromide, benzyldiethylsulfonium chloride, benzyldimethylsulfonium iodide, benzylethylvinylsulfonium chloride, tert-butyldimethylsulfonium chloride, tert-butylmethylpropylsulfonium iodide, trimethylsulfonium bromide, diisopentylmethylsulfonium iodide, diphenyl-2,5-xylylsulfonium bromide, cyclooctyldimethylsulfonium iodide, triphenylsulfonium iodide, trimethylsulfoxonium iodide, trimethylsulfoxonium bromide, trimethylsulfoxonium chloride, ethyldimethylsulfoxonium bromide, ferric chloride, stannic chloride, stannous chloride, manganese sulfate, zinc acetate, zinc benzoate, ferrous sulfate, stannous sulfate, stannic bromide, manganese iodide, zinc chloride, ferrous chloride, manganese acetate, stannous acetate and the like.

The amount of catalyst employed in the process of this invention is a catalytic amount, generally from 0.01 to 50 weight percent of the starting carbonate ester. In a presently preferred embodiment, from 0.1 to 10 weight percent of catalyst is employed.

Reaction conditions vary according to starting materials and catalyst. In general, the process is conducted at a temperature which will allow for decomposition of the cyclic carbonate ester to the desired vicinal epoxide without undesirable side reactions, for a time sufficient to provide essentially complete conversion.

The temperature employed in the process of this invention can be in the range of 25° to 300° C. In a presently preferred embodiment the temperature is in the range of 100° to 250° C.

The reaction time is generally within the range of 0.5 to 24 hours. It is preferred that the reaction time be in the range of 1.5 to 5 hours.

The process of this invention can be conducted at any suitable pressure, ranging from subatmospheric to atmospheric. It is preferred that the process be conducted at atmospheric pressure.

The process of this invention can be carried out in the presence or absence of a diluent. If desired, an inert diluent can be employed in an approximate amount ranging from 10 to 2000 weight percent of the starting carbonate ester. Suitable inert diluents include hydrocarbons such as benzene, toluene, decane and cyclohexane, ethers such as 1,2-dimethoxyethane and tetrahydrofuran and cyclic sulfones such as sulfolane. In a presently preferred embodiment the process of this invention is carried out in the absence of diluent in order to simplify recovery procedures.

The process of this invention can be carried out as a batch or continuous process.

The following examples illustrate the invention.

EXAMPLE I

A 50 ml round-bottom flask equipped with stirring means was charged with 30 g (0.294 mol) of propylene carbonate, i.e., the cyclic carbonate ester of 1,2-propanediol and 0.30 g of tetrabutylphosphonium chloride. The reaction vessel was equipped with a condenser operating at about 25° C. and a receiver connected thereto maintained at about −27° C. The reaction vessel was heated by an oil bath at 195-205° C. for 3 hours. The product recovered in the receiver at the end of the reaction period weighed 15.72 g while the residue in the reaction vessel weighed 0.82 g. Gas liquid chromatography (GLC) analysis indicted that the product in the receiver was 98.8 percent propylene oxide while the residue in the reaction vessel was 65 percent propylene carbonate. Thus, a propylene carbonate conversion of 98 percent with a 93 percent selectivity to propylene oxide was obtained.

EXAMPLE II

Two runs were carried out employing the same reaction system used in Example I in which 30 g of propylene carbonate was heated each time to 198°-208° C. for 3 hours in the absence of catalyst. Very minor amounts, 0.03 g and 0.06 g, of propylene oxide were recovered. The propylene carbonate was essentially unreacted.

It is evident from the above examples that thermal decomposition of propylene carbonate to propylene oxide is not substantially effected in the absence of a catalyst and that tetrabutylphosphonium chloride is an effective catalyst for this reaction.

EXAMPLE III

A series of runs was carried out using the compounds listed below to determine, qualitatively, whether propylene oxide was obtained from propylene carbonate. Reaction conditions were essentially the same as used in Example I, except that each run had a duration of 0.5 to 1 hour. Results of these runs are shown in the following table:

| Run | Compound quantity (g) | Decomposition to propylene oxide |
|---|---|---|
| 4 | $PdCl_2$, 1 | No |
| 5 | $Ag_2CO_3$, 1 | No |
| 6 | $CuCl_2 \cdot 2H_2O$, 1 | No |
| 7 | $Zn(benzoate)_2$, 0.3 | Yes |
| 8 | $Zn(acetate)_2$, 0.3 | Yes |
| 9 | ZnO, 0.3 | No |
| 10 | $Mo(CO)_6$, 0.3 | No |
| 11 | $MnSO_4$, 0.3 | Yes |
| 12 | $FeCl_3$, 0.3 | Yes |
| 13 | $NiSO_4$, 0.3 | No |
| 14 | $SnCl_4$, 0.3 | Yes |
| 15 | $SnCl_2$, 0.3 | Yes |

In each of the above runs which gave no indication of propylene oxide formation, the receiver was rinsed with a small volume of acetone to recover any material which might have been collected. The acetone wash liquid was analyzed by GLC for the presence of propylene oxide. In those runs showing negative results, no bubble formation was noted in the reaction vessel, as would be expected from the formation of carbon dioxide as the co-product with propylene oxide. Those runs showing positive results were observed to form bubbles during the reaction period.

Reasonable variations and modifications of this invention will be apparent to those skilled in the art in view of this disclosure. Such variations and modifications are within the scope and spirit of the disclosure.

What is claimed is:

1. A process for the preparation of a vicinal epoxide having 2 to 30 carbon atoms per molecule of the general formula

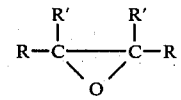

wherein each R and each R' are individually selected from the group consisting of hydrogen and hydrocarbyl radical groups having 1 to 10 carbon atoms and wherein both R' radicals in said epoxide can represent a divalent aliphatic hydrocarbon radical which together with the oxirane group in said epoxide can form a cycloaliphatic nucleus, which comprises heating the corresponding carbonate ester having the general formula

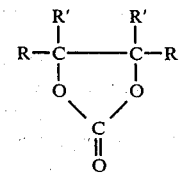

wherein R and R' are as defined above, in the presence of a catalytic amount of a metal salt catalyst selected from the group consisting of the halides, sulfates and carboxylates having 1 to 20 carbon atoms of tin.

2. The process of claim 1 wherein said carbonate ester is heated in the presence of said catalyst at a temperature in the range of 25° to 300° C.

3. The process of claim 1 wherein said catalyst is employed in an amount ranging from 0.01 to 50 weight percent of said carbonate ester.

4. The process of claim 1 wherein said carbonate ester is propylene carbonate.

5. The process of claim 1 wherein said catalyst is stannous chloride.

6. The process of claim 1 wherein said catalyst is stannic chloride.

* * * * *